United States Patent
Quillin

(10) Patent No.: US 6,899,903 B2
(45) Date of Patent: May 31, 2005

(54) COMPOSITION FOR CLEANSING THE SINUSES

(76) Inventor: Patrick Quillin, Box 130789, Carlsbad, CA (US) 92013

( * ) Notice: Subject to any disclaimer, the term of this patent is extended or adjusted under 35 U.S.C. 154(b) by 51 days.

(21) Appl. No.: 10/601,510

(22) Filed: Jun. 23, 2003

(65) Prior Publication Data

US 2004/0142046 A1 Jul. 22, 2004

Related U.S. Application Data

(60) Provisional application No. 60/391,022, filed on Jun. 25, 2002.

(51) Int. Cl.⁷ .......................... A61K 35/78; A61K 33/00
(52) U.S. Cl. ....................... 424/736; 424/725; 424/745; 424/618
(58) Field of Search ................................ 424/725, 736, 424/745, 618

(56) References Cited

U.S. PATENT DOCUMENTS

| | | | |
|---|---|---|---|
| 6,454,754 B1 * | 9/2002 | Frank | 604/500 |
| 2003/0003140 A1 * | 1/2003 | Domb et al. | 424/449 |
| 2003/0083212 A1 * | 5/2003 | Willard et al. | 510/137 |
| 2003/0225003 A1 * | 12/2003 | Ninkov | 514/23 |
| 2004/0009245 A1 * | 1/2004 | Vail et al. | 424/742 |
| 2004/0059281 A1 * | 3/2004 | Saemundsdottir | 604/11 |

FOREIGN PATENT DOCUMENTS

FR   2741535   *  5/1997

OTHER PUBLICATIONS

Barr, Stephen. "Homeopathy: The Ultimate Fake", http//www.quackwatch.com, 6 pages, downloaded from Web Aug. 1999.*
PROMT Product Alert bulletin entitled "AloeDent Aloe Vera Mouthwash", Sep. 11, 2000, vol. 30, No. 17, PROMT Abstract.*
Zimmer, M. Therapiewoche. 1985. vol. 35, No. 1 36, pp. 4024–4028, DRUGU Abstract enclosed.*
Vestweber et al. Arzmeimittel–Forschung. 1995. vol. 45, No. 9, pp. 1018–1020, CAPLUS Abstract enclosed.*

* cited by examiner

*Primary Examiner*—Christopher R. Tate

(57) ABSTRACT

A unique and synergistic composition is disclosed for cleansing the sinuses to reduce inflammation and improve breathing. The disclosure is also related to a composition for freshening and cleansing the sinus cavities and nostrils that includes a homeopathic ingredient and saline carrier solution. The disclosure is also related to the use of such composition to provide many anticipated and unexpected benefits that emanate from cleansing debris and microbes from the sinuses and nostrils.

3 Claims, 3 Drawing Sheets

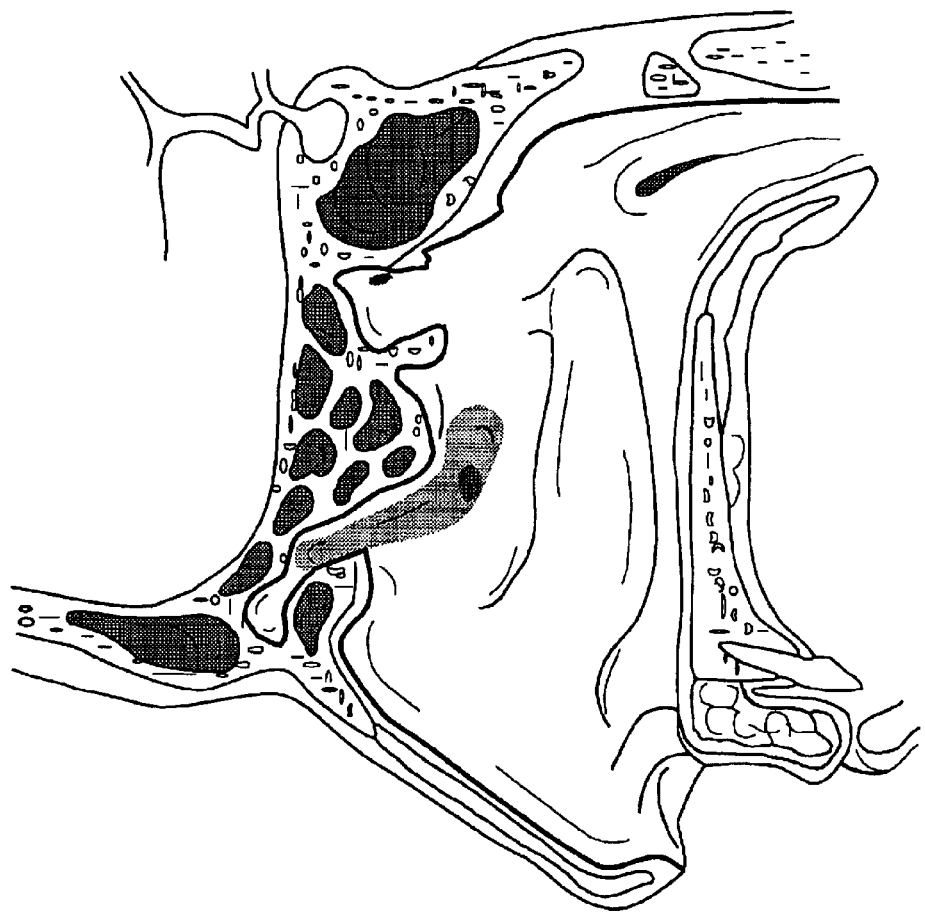
DRAWING 1
LATERAL WALL OF NASAL CAVITY

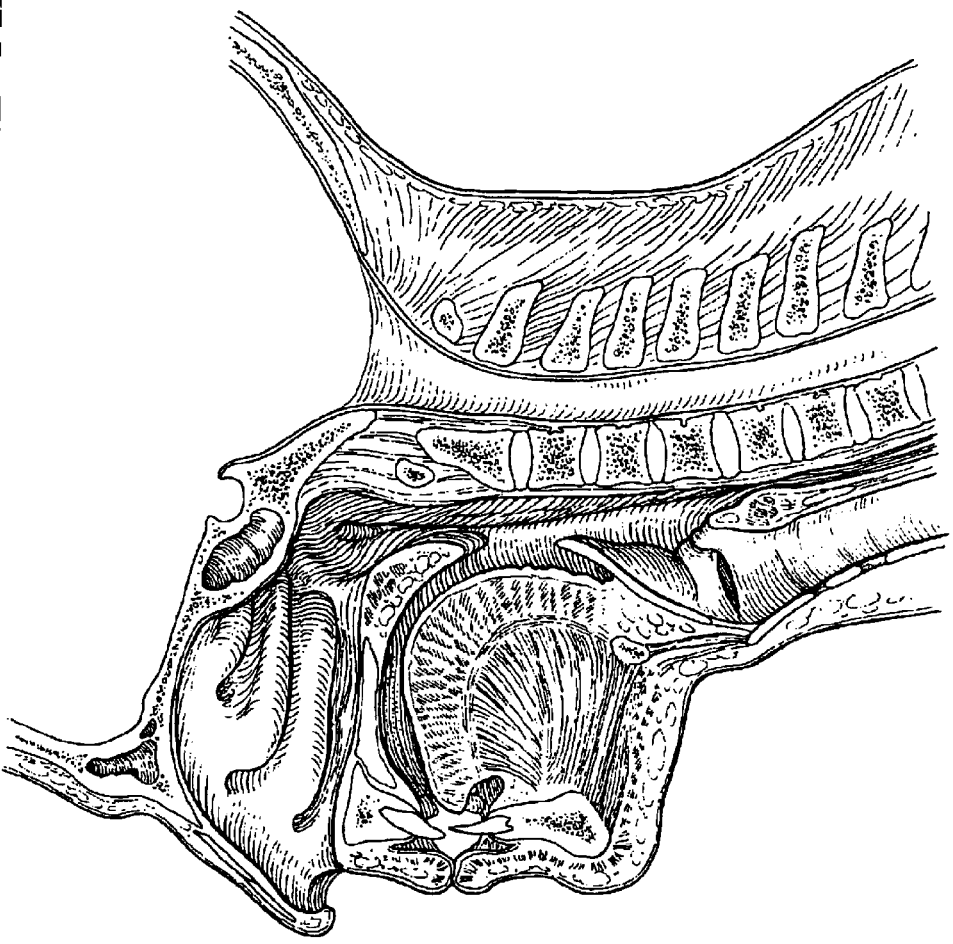

COMPOSITION FOR CLEANSING THE SINUSES

RELATED APPLICATIONS

This application claims the benefit of U.S. Provisional Application No. 60/391,022 filed on Jun. 25, 2002.

DESCRIPTION

1. Field of the Invention

The present invention relates to non-prescriptive compositions that have anti-microbial activity in cleansing the sinuses, and thus alleviating sinusitis, apnea, asthma, or other related upper respiratory infections and inflammatory conditions.

2. Background of the Invention

SINUS CAVITIES. The human head contains 4 sets of air-filled cavities known as the paranasal sinuses (Stedman's Medical Dictionary, 27th Edition, page 1644, 1999). The purpose of the sinuses appears to be both the filtration and warming of air as it enters the lungs. The location of the sinuses is from nostril entrance into the back of the throat and other passageways and cavities within the human head. Specifically, the four pairs of paranasal sinuses are the frontal sinuses (located in the forehead), the maxillary sinuses (located behind the cheekbones), the ethmoid sinuses (located between the eyes), and the sphenoid sinuses (located behind the eyes). Drawing 1 illustrates the lateral wall of the nasal cavity. Drawing 2 illustrates the lateral view of the human head and neck. Drawing 3 illustrates the cross sectional view of the human ear and auditory (or eustachian) tube leading to the sinuses. The purpose of these drawings is to emphasize the interconnectedness of the cavities in the human head. Infections in one area can lead to inflammation, pain, and further complications in another area of these paranasal sinuses and their adjoining bodies, such as the eyes, tonsils, adenoids, brain, and ears.

The membrane lining the sinuses secretes mucus, which contains antimicrobial agents (such as antibodies) and is sticky in texture to capture small particles and infective microbes. Other protective mechanisms in the human sinsuses include cilia, which are small hair-like projections located in the nostril which normally beat in unison to propel mucus outward, thus expelling infective microbes and other irritant particles. While the air we breath is filled with yeast spores, viruses, bacteria, and other irritants; a healthy human sinus passage possesses the host defense mechanisms to kill the invading microbes and wash away the irritants.

For healthy sinuses to be present, the mucous membranes must be intact, and the sinus passages must be open to allow drainage and circulation of air through the nasal passage. In fact, due to the inherent conditions of warmth, moisture, darkness, sugar substrate for microbes (mucus), and stagnation; the environment of the nasal passages is vulnerable to microbial infections. Sinusitis (inflammation of sinus passages), sleep apnea (cessation of breathing while sleeping), asthma (inflamed bronchial tubes leading to the lungs which causes labored breathing), otitis media (inflammation of the middle ear), headaches, snoring, and more can all be caused by infections and/or inflammation of the sinus passages.

Sinusitis

Sinusitis is an inflammation of the membrane lining one or more paranasal sinuses. According to the Center for Disease Control, thirty seven million cases of chronic sinusitis are reported annually, making this condition one of the most commonly reported reasons for patient visits to a family physician. There are three primary types of sinusitis:

a) acute (short in duration and infrequent in occurrence)

b) recurrent acute (occurs more often, but leaves no lasting damage to tissue)

c) chronic (lasting longer than 3 weeks, and may cause tissue damage)

Causes of Sinusitis

Most common cause of sinusitis is a viral cold that infects the upper respiratory tract and causes obstruction (online report from Etkins, et al., 1999, Nidus Information Services, Inc., Well-Connected Report: Sinusitis, Jun. 1999, www.well-connected.com). Once obstruction has occurred, the stagnated environment is hospitable for bacteria. Most common bacteria linked to acute sinusitis are *Streptococcus pneumoniae, H. influenzae* (common bacteria associated with respiratory infections in children), and *Staphyloccocus aureus*.

Fungi may also cause sinusitis. Researchers have found that 96% of chronic sinusitis patients have fungi present in their mucus smears (Mayo Clinic Proceedings, vol.74, p.877, 1999). Most common fungal species found in the nasal smears in this study included: *Alternaria, Aspergillus, Candida, Cladosporium, Fusarium,* and *Penicillium*. Fungal infections are more common in people with diabetes, leukemia, AIDS, conditions that impair the immune system, and those who consume medication that may impair immune functions, including corticosteroids. Fungal sinusitis usually occurs more often in warmer humid climates.

Chronic or recurrent acute sinusitis can become lifelong conditions that can damage surrounding tissues, including the creation of polyps, enlarged adenoids, cleft palate, or tumors.

Symptoms of Sinusitis

Nasal congestion and discharge which is thick and yellow or yellow-green are common symptoms of acute sinusitis. Pain in face and headache may also occur. Persistent cough may occur throughout the day. Fever may be present (Williams, M L, THE SINUSITIS HELP BOOK, Wiley, N.Y., 1998). Nasal congestion and obstruction are common in recurrent acute and chronic sinusitis, with symptoms lasting more than 2 months, even during non-allergy seasons. Chronic cough, post nasal drip, yellowish mucus discharge, and bad breath may result.

Depending on where the infections occurs, subsequent pain can occur. Frontal sinusitis causes pain across the lower forehead. Maxillary sinusitis may cause pain in the teeth, palate of the mouth, and cheek region.

Ethmoid sinusitis may cause pain behind the eyes. Sphenoid sinusitis may cause pain behind the eyes, across the forehead, or in the facial region (Rosin, D F, THE SINUS SOURCEBOOK, Contemporary, Chicago, 1998). Sinusitis of all forms is usually non-life threatening, yet can be debilitating with pain, side effects of medication, and the poor health that results from inability to breath fully.

Treatments of Sinusitis

Typical medical therapy for upper respiratory infections involves (Bruce & Grossan, THE SINUS CURE, Balantine, N.Y., 2001):

a) antimicrobials, such as antibiotics b) antisecretory agents, to shut down the flow of mucus c) anti-inflammatory agents, such as steroids (i.e. prednisone), to reduce the swelling from the infection Home remedies for sinusitis include steam inhalation and warm compresses over the region to relieve discomfort (MacFarlane, M., THE SINUS HANDBOOK, USRP, Encinitas, Calif., 1997). Many over-the-counter (OTC) preparations are available, including decongestants that are delivered as tablets, sprays, or vapors. Prescription drugs and surgery are expensive and ladened with side effects and risks.

A Summary of the Properties of Ingredients of the Composition *Baptisia Tinctoria*

This agent is a homeopathic ingredient. The word "homeopathy" derives from the Greek word homoios meaning "similar" and pathos, meaning "suffering". Based on the principle of "like cures like", homeopathic remedies are dilutions of natural agents, including extracts from plants, animals, and minerals. Homeopathy was founded in the late 18$^{th}$ century in Germany by a physician, Samuel Hahnemann. Dr. Hahnemann found that by ingesting extract of cinchona, which contains quinine that is used to cure malaria, he was able to develop the well-known symptoms of malaria. Hence, the expression "like cures like" (ALTERNATIVE THERAPIES, p. 272, Future Medicine Publishing, Puyallup, Wash., 1993). Homeopathy uses an official compendium, HOMEOPATHIC PHARMACOPOEIA OF THE UNITED STATES, and has several main principles:

a) Like cures like, law of similars b) The more a remedy is diluted, the greater its potency, law of infinitesimal dose c) An illness is specific to the individual While most of modern allopathic drugs block biochemical pathways, homeopathy uses a more subtle energy system with no known side effects or deaths in its 180 year history. Over a half a billion people around the world use homeopathy as adjunctive or primary care for illness. The World Health Organization has cited homeopathy as one of the systems of traditional medicine that should be integrated worldwide to provide adequate global health care. Essentially, homeopathic remedies are extremely dilute mixtures of the substance that would induce the same symptoms one is attempting to cure. A 12x remedy, as is found in this invention, has been diluted $10^{12}$ times. Homeopathic remedies are diluted then shaken (succussion). *Baptisia tinctoria* is considered to be antimicrobial in homeopathic medicine. The United States Food and Drug Administration recognizes homeopathic remedies as official drugs and regulates their manufacturing, labeling, and dispensing; although homeopathic remedies are not prescription drugs.

OREGANO is an antimicrobial herb with GRAS (generally regarded as safe) status with the Food and Drug Administration.

COLLOIDAL SILVER also has GRAS status and is a suspension of silver particles in water solution that exhibits antimicrobial activity.

GRAPEFRUIT SEED EXTRACT has GRAS status and is an extract from grapefruit seed with antimicrobial activity.

BENZALKONIUM CHLORIDE is an FDA-approved preservative with antimicrobial value.

SUMMARY OF THE INVENTION

It is, therefore, one of the principle objects of the present invention to eliminate microbes in the sinus passages that may cause inflammation and infections.

Another object of the present invention is to provide a composition which may be conveniently introduced through the nose with a simple plastic squeeze bottle which causes no discomfort to the user.

A further object of the present invention is to provide a simple, non-toxic, non-prescription, and effective means at reducing pathogenic microbes, dust, pollen, and general debris in the sinus passages for the immediate and residual benefits of improved health and reduced symptoms.

These and additional objects are attained by the present invention which, in the broadest sense, comprises a collection of synergistic and non-toxic agents that cleanse the sinuses, eliminate infectious agents, reduce swelling, and accelerate recovery from sinusitis without significant side effects.

Various additional objects and advantages of the present invention will become apparent from the following detailed description.

DESCRIPTION OF DRAWINGS

Drawing 1: Lateral wall of nasal cavity.

Drawing 2: Lateral view of human head and neck

Drawing 3: Cross sectional view: human ear and auditory tube leading to sinuses

All drawings are included to show the depth and scope of the sinus cavities, their vulnerability, and the value of using my invention for regular cleansing of debris and infectious microbes from the sinuses.

DETAILED DESCRIPTION OF THE PREFERRED EMBODIMENT

The present invention is a liquid or vapor that is inhaled, squirted, or vaporized into the nostrils and sinus cavities. It is of particular utility for use by persons who suffer from sinusitis, common colds, work around dust or fumes, travel by airlines often, or suffer from pollen and other allergies.

The composition includes a carrier, which can be water or dilute saline (salt water) solution. Saline solution is preferred since it confers an additional mild antimicrobial activity to the composition. Saline mists are commonly used by people with sinus congestion. Saline solutions are commonly sold at pharmacies as OTC preparations for sinus problems. Saline solutions are safe, but not sufficiently antimicrobial to resolve most cases of chronic sinusitis. Isotonic saline solutions, as found in this invention, attempt to mimic the concentration of salt in human bodily fluids, hence they usually do not irritate the sinus membranes.

Control and/or elimination of infective microbes in the sinuses can be achieved by using the ingredients listed in this patent: *Baptisia tinctoria* 12x, colloidal silver, grapefruit seed extract, and oregano. Other agents that may be of benefit in this nasal solution include, but are not limited to: oil of peppermint, spearmint, eucalyptol, methyl salicylate, and various other non-toxic, non-prescription antimicrobials.

The delivery method used for this composition can vary from plastic squeeze bottle, which squirts the composition into the sinus cavities, to an atomizer, or pump mister, which sprays fine particles of the composition into the sinuses.

No unusual discomfort for the user has been experienced in the 4000 people who have used this product. Many of the users have been afflicted with acute chronic sinusitis, hence inflamed mucus membranes can be fragile, even when saline solution is sprayed into the nose.

There are numerous advantages from the use of the composition. Nearly forty million Americans suffer from chronic sinusitis. Some of these people take prescription drugs, such as antibiotics, which may invite a fungal infection. Some of these people may use systemic steroid medication, which suppresses immune functions and has long term complications. Some of these people may use OTC products which induce drowsiness and could raise the risk for automobile accidents or other. By using the composition, these sinus sufferers can avoid the many side effects, high cost, and ineffectiveness that are often associated with traditional treatments for sinusitis.

Selected Case Studies Showing Successful Use of the Composition

Person 1: Male 51 years old. Experienced sinus congestion periodically for the past 40 years. Experienced blood in the nose for the past 10 years. Problem would worsen in certain climates and at certain times of the year, but never got better. Tried various over the counter sinus preparations, changed diet, took nutrition supplements-all to no avail. Used the composition for one week and began to feel significant relief. Blood in nose stopped. Congestion cleared up substantially. With continued use, claims breathing better than in the past 40 years.

Person 2: Female 62 years old. Experienced sinus congestion for 30 years, including regular use of over the counter sinus medications. Had undergone sinus surgery, which did not clear the problem. Began using the composition and felt substantial immediate relief. After 4 days of use, found green and yellow fungal balls expelled in mucus. Continued use of this product provides significant relief from sinus congestion and easier breathing.

Person 3: Female 65 years old. Experienced sinus congestion for 40+ years. Used many prescription and non-prescription medications for minor temporary relief of symptoms. Within 2 days of using the composition reported major improvements in breathing.

One individual who used the composition cancelled sinus surgery, due to the dramatic improvement from using the composition. Some individuals who used the composition have been able to cease dependency on inhalers, OTC, and prescription medication. Others have found improvements in apnea, snoring, sinus headaches, and asthma. Some individuals who used the composition have reported reduction in the incidence of colds after frequent airplane trips. If one examines a typical home air filter unit in the air conditioning or furnace, it is easy to see the pollen, dust, and debris that can accumulate in the sinus passages. Since the nose and sinuses work in a similar fashion by filtering the air entering the lung passage, regular cleansing of the sinuses with the composition has been shown to improve many aspects of health, including reduction in sinusitis and easier breathing.

EXAMPLE FORMULA FOR COMPOSITION

The following formula provides a representative example of the composition, including both percentages and amount used in a typical 4 ounce bottle:

| INGREDIENT | common | concentration | ranges claimed |
|---|---|---|---|
| Baptisia tinctoria 12x | 99.2% | 117.33 milliliters | 1% to 99% |
| Colloidal silver | 0.565% | 0.668 ml | 0.01% to 10% |
| Grapefruit seed extract | 0.07% | 0.0834 ml | 0.01% to 5% |
| Oregano juice | 0.07% | 0.0834 ml | 0.01% to 5% |
| Sodium chloride (salt USP) | 0.75% | 887.1 mg | |
| Benzalkonium chloride | 0.01% | 0.023656 ml | |
| Sodium hydroxide to adjust pH to 6.2 (less than 1 ml) | | | |

The above listed formula for the composition has undergone extensive testing in 4000 users and has demonstrated exceptional effectiveness at cleansing the sinuses, reducing symptoms of sinusitis, and bringing about easier breathing.

I claim as my invention:

1. An aqueous solution for treating sinusitis adapted to be sprayed into a nasal cavity, said solution comprising:

a) *Baptisia tinctoria* 12x from 1% to 99%, by vol, b) colloidal silver from 0.01% to 10%, by vol, c) grapefruit seed extract from 0.01% to 5%, by vol, d) oregano juice from 0.01% to 5%, by vol.

2. A solution as defined in claim 1 which further incorporates sodium chloride from 0.01% to 5%, by wt.

3. A solution as defined in claim 1 which further incorporates benzalkonium chloride from 0.01% to 5%, by vol.

* * * * *